US007753864B2

(12) United States Patent  
Beckwith et al.

(10) Patent No.: US 7,753,864 B2  
(45) Date of Patent: Jul. 13, 2010

(54) FOOT SUPPORT DEVICE

(75) Inventors: Tanya L. Beckwith, Inver Grove Heights, MN (US); Maria T. Mann, Woodbury, MN (US); Jeffrey L. Wieringa, West Lakeland, MN (US); Wayne K. Dunshee, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 142 days.

(21) Appl. No.: 11/615,515

(22) Filed: Dec. 22, 2006

(65) Prior Publication Data

US 2008/0154166 A1 Jun. 26, 2008

(51) Int. Cl.  
A61F 5/00 (2006.01)  
A61F 5/37 (2006.01)

(52) U.S. Cl. .................. 602/23; 602/5; 602/27; 128/882

(58) Field of Classification Search .......... 602/23, 602/29, 5, 28, 27; 2/239, 240, 311, 313, 2/318; 128/882, 100.1, 105.1, 883; 482/79, 482/124, 907; 36/145, 166, 169, 170; 119/726, 119/814, 818, 863, 816, 856; D24/190; 224/222, 224/267, 578, 579, 586  
See application file for complete search history.

(56) References Cited

U.S. PATENT DOCUMENTS

| 3,527,209 | A | * | 9/1970 | Baker ..................... 602/28 |
| 4,598,702 | A |   | 7/1986 | Lilla |
| 4,905,713 | A |   | 3/1990 | Morante |
| 5,219,324 | A |   | 6/1993 | Hall |
| 5,256,119 | A | * | 10/1993 | Tudor ..................... 482/74 |
| 5,399,155 | A | * | 3/1995 | Strassburg et al. ....... 602/28 |
| 5,554,107 | A |   | 9/1996 | Shannahan |
| 5,611,770 | A |   | 3/1997 | Tesch |
| 5,718,673 | A | * | 2/1998 | Shipstead ............... 602/27 |
| 5,776,090 | A |   | 7/1998 | Bergmann |
| 5,799,659 | A |   | 9/1998 | Stano |
| 5,843,010 | A | * | 12/1998 | Bodmer ................. 602/27 |
| 5,897,520 | A |   | 4/1999 | Gerig |
| 6,019,741 | A | * | 2/2000 | Prieskorn ................ 602/5 |
| 6,267,742 | B1 |   | 7/2001 | Krivosha et al. |
| 6,499,485 | B1 |   | 12/2002 | Pepera |
| 6,602,216 | B1 |   | 8/2003 | Nordt, III |
| 6,641,550 | B1 |   | 11/2003 | Johnson |
| 6,695,797 | B2 |   | 2/2004 | Trieloff |
| 6,755,798 | B2 |   | 6/2004 | McCarthy et al. |
| 6,793,636 | B1 |   | 9/2004 | Pepera |

(Continued)

*Primary Examiner*—Patricia M Bianco  
*Assistant Examiner*—Victoria Hicks  
(74) *Attorney, Agent, or Firm*—Robert H. Jordan; Lisa P. Fulton

(57) ABSTRACT

A device for treatment of plantar fasciitis and/or Achilles tendonitis comprises (a) a calf strap removably engagable to the calf of a leg, (b) a foot assembly removably engagable to the foot of the leg such that when the device is worn the assembly can be positioned proximate to the ball of the foot intermediate to the midfoot and forefoot areas of the foot to secure it to the foot, and (c) a substantially inelastic tension member connectable between the calf strap and the foot assembly in a tensioned manner such that when the device is worn the plantarflexion of the ankle is limited such that the plantar surface of the foot is held in a neutral to slight dorsiflection.

10 Claims, 1 Drawing Sheet

U.S. PATENT DOCUMENTS

| | | | |
|---|---|---|---|
| 7,261,679 B2 * | 8/2007 | Sload | 482/124 |
| 2002/0068667 A1 * | 6/2002 | Strachan | 482/124 |
| 2004/0215123 A1 | 10/2004 | Slautterback et al. | |
| 2005/0054963 A1 | 3/2005 | Ingimundarson | |
| 2006/0064048 A1 | 3/2006 | Stano | |

* cited by examiner

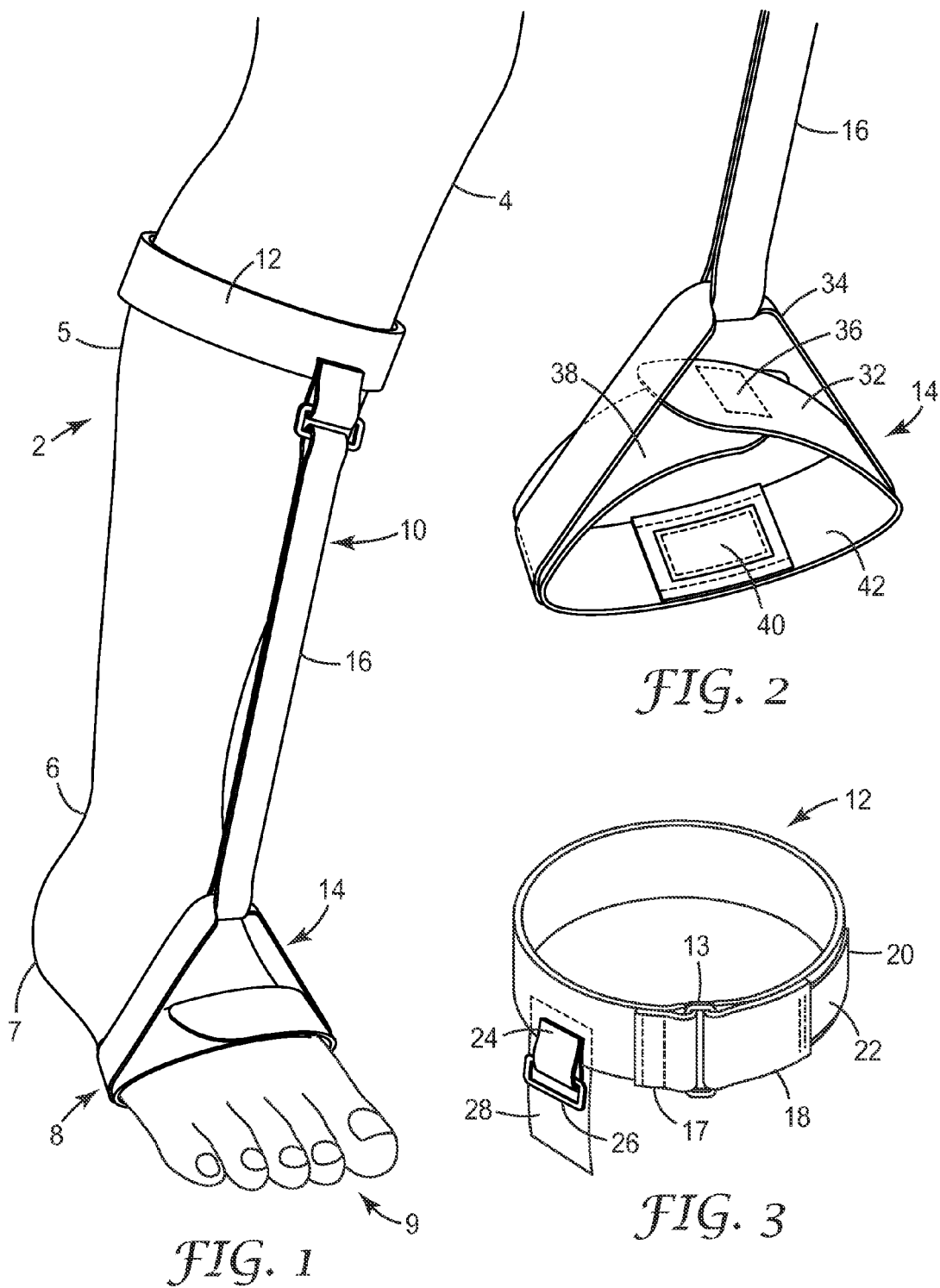

FOOT SUPPORT DEVICE

FIELD OF THE INVENTION

The present invention relates to an orthotic device, specifically a night splint for treating and facilitating in the treatment of the pain in the foot and heel caused by contracture of the plantar fascia and/or the Achilles tendon.

BACKGROUND

The human foot and ankle contain 26 bones and more than 100 muscles, tendons, and ligaments. This complex structure takes the brunt and impact of every step experienced by an individual. It is likely that the single largest source of complaint for foot ailments is related to heel pain.

One source of heel pain commonly observed is due to a condition known as recalcitrant plantar fasciitis. Plantar fasciitis occurs in the plantar fascia, a fibrous membrane disposed longitudinally across the bottom of the foot. The plantar fascia is attached at the heel bone (to the inner tubercle of the os calcis). The plantar fascia becomes broader and thinner as it extends longitudinally across the bottom of the foot, eventually dividing near the heads of the metatarsal bones into five processes, one for each of the five toes. The strongest ligament in the body, the plantar fascia's purpose is to protect the softer muscles and tissues of the bottom of the foot from injury, as well as to help maintain the integrity of the foot structure itself.

If the fascia becomes stretched or strained, the arch area becomes tender and swollen as well as the area about the heel bone. This inflammation is called plantar fasciitis and is typically painful from the heel throughout the arch up into the Achilles tendon. Patients suffering from this condition usually have relatively tight and inflexible heel cords, sometimes referred to as Achilles tendon tightness. When the heel cord is tight, it causes compensation in the foot with over pronation of the foot during weight bearing. The pain is consistently worse when you first get up in the morning and at the end of the day. The pain usually lurks in the heel pad and may include the arch ligament. A common tendency is to ignore the symptoms of the pain at first.

Plantar fasciitis is often caused by contracture of the Achilles tendon and the plantar fascia, which can occur at night during sleep, or during daytime inactivity. The Achilles tendon, the strongest and thickest tendon in the human body, begins at or about the middle of the posterior side of the leg extending downward towards the heel, narrowing as it progresses towards its point of insertion at the posterior surface of the os calcis. When an individual is standing, walking, running, or even sitting in a position in which the feet are in contact with the floor or other surface, both the plantar facia and the Achilles tendon are extended to varying degrees depending of course on the nature and intensity of the activity. During sleep, an individual has a natural tendency to plantar-flex the ankle joint beyond the position which is normal during walking, standing, or sitting with one's feet on the floor. Plantarflexion is when the bottom of the foot is extended so as to form an angle with the lower leg of greater than 90°, i.e., extend such that the forefoot moves away from the body. Dorsiflexion is the opposite motion, when the foot is moved to a position in which the bottom of the foot forms an angle with the lower leg of less than 90°, i.e., such that the top of the foot moves toward the body.

Another condition, Achilles tendonitis can result from overuse of the tendon in sports activities, and can also result from a number of inflammatory diseases, of which rheumatoid arthritis is one.

As a result of plantar flexion during the night, the plantar facia and the Achilles tendon contract from their size and dimension normal to the walking, standing, or sitting positions. Upon arising, the plantar facia and the Achilles tendon are once again extended and stretched when the feet and ankles resume a normal position associated with walking or standing. Typically, it is when an individual arises following sleep or a period of extended recumbency that the effects of heel pain associated with plantar fasciitis, with, or without the associated Achilles tendon contracture, are observed, and in a significant number of cases the pain has been described as substantial.

For some time, a common method of treatment of plantar fasciitis and Achilles tendonitis has been the use of a night splint. The night splint typically consists, essentially, of a boot-like structure which is strapped to a patient's lower leg and foot, holding the foot relative to the lower leg in a position such that the ankle joint is held in slight dorsiflexion. In so doing, both the plantar fascia and the Achilles tendon are slightly extended and are not allowed to contract during the night. The use of night splints together with the variety of other elements of treatment including anti-inflammatory medications, physical therapy, and foot cushions for use during the daytime, has proved beneficial in the treatment of plantar fasciitis.

Various braces and splints, sometimes referred to as night splints, are advertised for treatment of plantar fasciitis and/or Achilles tendonitis. These devices typically consist of a molded splint or a combination of molded plastic and metal framework, with the dorsiflexion set at, for example, about 5°. Illustrative examples are disclosed in U.S. Pat. No. 5,399,155 (Strassburg et al.), U.S. Pat. No. 5,718,673 (Shipstead), U.S. Pat. No. 5,799,659 (Stano), U.S. Pat. No. 5,897,520 (Gerig), U.S. Pat. No. 6,019,741 (Prieskom), U.S. Pat. No. 6,267,742 (Krivosha et al.), U.S. Pat. No. 6,602,216 (Nordt, III), U.S. Pat. No. 6,695,797 (Trieloff), and U.S. Pat. No. 6,755,798 (McCarthy et al.), and U.S. Patent Application Publication Nos. 2004/0215123 (Slautterback et al.) and 2006/0064048 (Stano).

To treat plantar fasciitis or Achilles tendonitis, it is necessary to use considerable force to counteract the strong muscles and tendons of the lower leg and foot to maintain the affected foot and ankle in the desired dorsiflexion. If this force is applied improperly, pressure points can result, with resulting discomfort and complications for some patients. Some patients have reduced blood circulation or sensation in the feet, such as patients with diabetes, vascular insufficiency, polio, stroke, trauma, or neurological problems. In such patients, if they need to use a night splint for treatment of plantar fasciitis, it is important to minimize the pressure points exerted by the night splint on the patient's foot, while still exerting the necessary force on the foot and lower leg structure. The night splint must also not bruise or scratch the collateral leg during sleep, must not soil or tear bedding, and must be compatible with a sleeping partner.

The need exists for improved devices for treating plantar fasciitis and/or Achilles tendonitis.

BRIEF SUMMARY OF THE INVENTION

The present invention provides a device and method for treating pain the foot and heel caused by contracture of the plantar fascia and/or the Achilles tendon.

When worn as described herein, the device of the present invention maintains the plantar fascia and other structures on the plantar surface of the foot in a neutral to slight dorsiflexion under application of static tension. This tension is of sufficient force so as to prevent the ankle from adopting a position of plantarflexion. As a result, after removal of the device by the wearer, and upon bearing weight on the effected foot, the plantar fascia will not be placed in pathologic tension thus reducing and/or eliminating pain.

In brief summary, the device of the invention comprises:
(a) a calf strap removably engagable to the calf of a leg;
(b) a foot assembly removably engagable to the foot of the leg such that when the device is worn the assembly can be positioned proximate to the ball of the foot intermediate to the midfoot and forefoot areas of the foot to secure it to the foot; and
(c) a substantially inelastic tension member connectable between the calf strap and the foot assembly in a tensioned manner such that when the device is worn the plantarflexion of the ankle is limited such that the plantar surface of the foot is held in a neutral to slight dorsiflection.

Briefly summarizing, the method of the invention comprises applying a device as described herein so as to maintain the plantar fascia and other structures on the plantar surface of the foot in a neutral to slight dorsiflection, said device comprising.

Devices of the invention provide several advantages over prior art devices. They are convenient and easy to use. Lightweight and non-obtrusive, they are comfortable to wear, making them easier to tolerate and use during moments of rest or sleep periods. In addition to providing efficacious results, the device will not bruise or scratch the affected leg or the collateral leg during sleep, will not soil or tear bedding, and is compatible with a sleeping partner.

BRIEF DESCRIPTION OF THE DRAWINGS

The invention will be further explained with reference to the drawing, wherein:

FIG. 1 is a perspective view showing one embodiment of a device of the invention applied to a leg and foot of an individual using the device;

FIG. 2 is a perspective view of a portion of one embodiment of a device of the invention; and FIG. 3 is a perspective view of a portion of one embodiment of a device of the invention.

These figures, which are idealized, are not to scale and are intended to be merely illustrative and non-limiting.

DETAILED DESCRIPTION OF ILLUSTRATIVE EMBODIMENTS OF THE INVENTION

Illustrative embodiments of the invention will be explained with reference to the drawings wherein similar reference characters denote similar elements throughout the various views.

Turning to FIG. 1, device 10 is shown applied to one leg 2 of an individual. The knee 4, calf 5, ankle 6, heel 7, foot 8, and toes 9 of the affected leg 2 are shown. Device 10 comprises:
(a) a calf strap 12 removably engaged to the calf 5;
(b) a foot assembly 14 removably engaged to the foot 8 wherein the assembly 14 is positioned proximate to the ball of the foot 8 intermediate to the midfoot and forefoot areas; and
(c) a substantially inelastic tension member 16 connected between the calf strap 12 and the foot assembly 14 in a tensioned manner such that the plantarflexion of the ankle 6 is limited such that the plantar surface of the foot 8 is held in a neutral to slight dorsiflection.

When the device is used, the calf strap 12 is engaged to leg. Typically, it will be engaged with the upper portion of the shin of the leg, preferably anywhere above the thickest portion of the calf muscle and below the knee 4.

When the device is used, the foot assembly 14 is engaged to the foot 8. Typically the foot assembly 14 is positioned proximate to the ball of the foot 8 intermediate to the midfoot and forefoot areas of the foot, i.e., at the distal end of the metatarsal bones. When positioned in this fashion, sufficient tension can be applied to limit plantarflexion of the foot without incurring undue and uncomfortable localized pressure at the location of the foot assembly or at the location of the calf strap. Also, because the pressure is applied to the metatarsal bones, uncomfortable pressure is not applied to the toes, i.e., the phalanges.

The tension member 16 is connected to the calf strap 12 and foot assembly 14. The tension member is a dimensionally stable, substantially inelastic, but preferably flexible member. When connected to the device 10 is worn, the tension member 16 limits the maximum distance between the affected leg and foot, thereby limiting the plantarflexion of the ankle 6. The plantar surface or bottom of the foot 8 is held in a position of neutral or slight dorsiflection.

The calf strap 12 is releasably engagable with the calf. It typically comprises a flexible belt or strap which can be wrapped around the affected leg and secured. Examples include leather belts, fiber straps, etc. The calf strap 12 should be long enough to reach securely around the affected leg and is preferably wide enough to permit comfortable wear. An illustrative example is a cotton or nylon strap that is about 1.5 to about 2.5 inches (about 3.8 to 6.4 cm) in width. Narrower straps may tend to localize pressure uncomfortably on the leg.

An illustrative calf strap 12 is shown in FIG. 3 wherein the strap 12 comprises a buckle 13 secured at one end 17 through which the other end 18 of the strap 12 may be passed and then secured to the surface 20 with a closure tab 22. For example, surface 20 and closure tab 22 may comprise with mating hook and loop materials. Other illustrative examples of fastening structures which may be used include but are not limited to adhesive, buckle, snap button, or slot button.

The calf strap 12 is preferably flexible enough to wrap comfortably around the affected leg 2, but should be sufficiently dimensionally stable and resistant to folding or wrinkling that it is does not become uncomfortable.

The calf strap 12 is adapted for the tension member 16 to be connected thereto. Such connection should be sufficiently strong to apply the necessary force to maintain the foot and ankle in position and resist the tendency for plantarflexion. In some embodiments (not shown), the tension member 16 may be permanently connected to the calf strap such as by stitching, riveting, or other mechanical connection. In a preferred embodiment shown in FIG. 3, the calf strap 12 comprises a tab 24 and a buckle 26 attached to the tab 24. In this preferred embodiment, the calf strap further comprises an optional cushion tab 28 disposed between the surface of the leg to which the device is applied and the buckle 26. In this preferred embodiment, the tab 24 is attached to the lower portion of the backing of the calf strap, i.e., that portion located nearer the foot of the affected leg and opposite the side nearer the knee of the affected leg. It has been observed that this configuration tends to reduce the tendency of the calf strap to roll over as compared to embodiments where the tab is attached toward the upper potion of the calf strap, i.e., nearer the knee. As a result, such embodiments of the device are more comfortable to wear.

The tension member 16 is substantially inelastic. It may be releasably connected to both the calf strap 12 and the foot assembly 14, or it may be permanent connected to one and releasably connected to the other. In some embodiments, the tension member 16 may be permanently connected to both the calf strap and to the foot assembly 14 and be made up of separable components, e.g., mating hook and loop material that are engaged when the device is worn. In a typical embodiment, the tension member will be a strap that is from about 1 to about 1.5 inches wide (2.5 to 3.8 cm) though other materials may be used if desired. For example, a suitable string or cord may be used if desired.

A preferred embodiment of foot assembly 14 is shown in FIG. 2 wherein the foot assembly 14 comprises a foot strap 32 which is adapted to releasably engage with the affected foot (not shown) and a yoke strap 34 which connects the tension member 16 to the foot assembly 14.

In the embodiment show, the foot strap 32 comprises a elongated piece of flexible material that can be wrapped around the foot to the secure the foot assembly thereto and then secured. The foot strap 32 is preferably flexible and conformable to improve comfort. The foot strap 32 may be secured with any of many known closures including but not limited to hook material, mated hook and loop closure, adhesive, buckle, snap button, or slot button. Use of a hook material 36 that will releasably engage with the outer surface 38 of the foot strap 32 is a preferred embodiment as it is easily donned and released and permits easy adjustment of the foot assembly 14 to ensure comfortable wear.

The foot strap 32 should be long enough to wrap around the ball of the foot and be secured. In a typical device it will be about 10 to about 15 (25 to 38 cms) inches in length though it will be understood that shorter or longer straps may be used depending upon the size of the patient's foot. The foot strap should be wide enough and thick enough to cushion the stabilizing tension on the patient's foot so as to avoid discomfort. In a typical device it will be about 2 to about 3 inches (5 to 8 cm) wide, though foot straps having narrower or wider widths may be used if desired. An illustrative example of a suitable material for use in the foot strap is Breath-O-Prene® fabric, which is commercially available from AccuMED Technologies, Inc. of Buffalo, N.Y.

The yoke strap 34 is connected to the foot strap 32. In the embodiment shown, it is attached to the outer surface of the foot strap 32 and extends completely around so as to cross under the foot (not shown) when the device is worn. The yoke strap is preferably an inelastic material to permit consistent tension when the device is worn. In the embodiment shown, the yoke strap 34 is permanently attached to the tension member 16. As will be understood, if desired it can be releasably connected thereto.

In the embodiment shown in FIG. 2, the foot assembly 14 includes an optional pad 40 located on the inside surface 42 disposed in a location to be positioned proximately to the bottom side of the foot (not shown) when the device is worn. The pad 40 may be used to provide additional cushioning of the pressure against the foot. The pad 40 may be provided with adhesive or hook material to engage with a sock to provide additional stability to the device if desired.

In some embodiments (not shown), the foot assembly may further comprise a skid resistant material on its bottom, outer surface.

With respect to the above description, it is to be realized that the optimum dimensional relationships for the parts of the invention, to include variations in size, materials, shape, form, function and manner of operation, assembly and use, are deemed to be within the expertise of those skilled in the art, and all equivalent structural variations and relationships to those illustrated in the drawings and described in the specification are intended to be encompassed by the present invention.

What is claimed is:

1. A device for limiting plantarflexion of an ankle thereby maintaining the plantar fascia in a neutral to slight dorsiflection, said device comprising:
   (a) a calf strap removably engagable to the calf of a leg;
   (b) a foot assembly removably engagable to the foot of said leg such that when the device is worn said assembly can be positioned proximate to the ball of said foot; and
   (c) a substantially inelastic tension member connectable between said calf strap and said foot assembly in a tensioned manner such that when said device is worn the plantarflexion of said ankle is limited such that the plantar surface of said foot is held in a neutral to slight dorsiflection;
   wherein said foot assembly comprises a flexible and conformable foot strap and an inelastic yoke strap which is adapted to engage with said tension member, and said yoke strap is attached to the outer surface of said foot strap and extends completely around so as to cross under the foot when the device is worn.

2. The device of claim 1 further comprising a loop attached to said calf strap wherein said loop and said tension member are adapted to engage with one another to connect said tension member to said calf strap.

3. The device of claim 1 wherein said loop is attached to the bottom edge of said calf strap.

4. The foot support system of claim 1 wherein said calf strap has a first end and a second end with a first fastener and a second fastener attached respectively thereto for allowing selective closing thereof upon said.

5. The device of claim 1 wherein said foot strap has a first end and a second end with a first fastener and a second fastener attached respectively thereto for allowing selective closing thereof around said foot.

6. The device of claim 1 further comprising a pad on the interior portion of said foot strap proximate the underside of the foot.

7. The device of claim 1 wherein said tension member is releasable from at least one of said calf strap and said foot assembly.

8. The device of claim 1 wherein said tension member is permanently attached to said foot assembly.

9. The device of claim 1 wherein said foot strap is elastic.

10. A method of limiting plantarflexion of an ankle thereby maintaining the plantar fascia in a neutral to slight dorsiflection, said method comprising:
   (a) engaging a calf strap to the calf of a leg;
   (b) engaging a foot assembly to the foot of said leg wherein said assembly is positioned proximate to the ball of said foot intermediate to the midfoot and forefoot areas of said foot a foot assembly removably engagable to the foot of said leg such that when worn, said assembly can be positioned proximate to the ball of said foot; and
   (c) connecting a substantially inelastic tension member between said calf strap and said foot assembly in a tensioned manner such that the plantarflexion of said ankle is limited such that the plantar surface of said foot is held in a neutral to slight dorsiflection;
   wherein said foot assembly comprises a flexible and conformable foot strap and an inelastic yoke strap which is adapted to engage with said tension member, and said yoke strap is attached to the outer surface of said foot strap and extends completely around so as to cross under the foot when worn.

* * * * *

UNITED STATES PATENT AND TRADEMARK OFFICE
CERTIFICATE OF CORRECTION

PATENT NO. : 7,753,864 B2  
APPLICATION NO. : 11/615515  
DATED : July 13, 2010  
INVENTOR(S) : Tanya L. Beckwith It is certified that error appears in the above-identified patent and that said Letters Patent is hereby corrected as shown below:

In the Specification

<u>Column 2</u>
Line 38, delete "(Prieskom)," and insert -- (Prieskorn), --, therefor.

Signed and Sealed this
Thirtieth Day of July, 2013

Teresa Stanek Rea
*Acting Director of the United States Patent and Trademark Office*